United States Patent [19]

Vielkind

[11] Patent Number: 5,605,831
[45] Date of Patent: Feb. 25, 1997

[54] HUMAN MELANOMA CELL SPECIFIC ANTIGENS AND ANTIBODIES

[75] Inventor: Juergen R. Vielkind, Vancouver, Canada

[73] Assignee: University of British Columbia, Vancouver, Canada

[21] Appl. No.: 829,855

[22] Filed: Jan. 31, 1992

[51] Int. Cl.$^6$ .......................... C07K 16/44; A61K 38/03; G01N 33/53

[52] U.S. Cl. .......................... 435/344; 514/16; 530/387.9; 530/387.7; 530/391.8; 436/547; 435/344.1

[58] Field of Search .............................. 530/387.7, 391.3, 530/391.7; 514/16; 436/547; 435/240.27

[56] References Cited

U.S. PATENT DOCUMENTS 4,590,071  5/1986  Scannon et al. ..................... 424/130.1

OTHER PUBLICATIONS

Real et al. Cancer Research 46: 4726–4731 1986.
Carrasgrullo et al. Cancer Treatment Reports 68(1)p. 317 1984.
The American Journal of Pathology, 123(2) p. 195 1988.
Savier et al. Clinical Chemistry 27/11 1797–1806 1981.
Wittbrodt et al. Nature vol. 341 415–421 1989.
Parker et al. Biochemistry vol. 25, 19, 1986 Lerner Nature vol. 299 1982 594.
Staerz et al. PNAS. vol. 83 1453 1986 Waldman Science 252, 1657 1991.
Hird et al. Genes and Cancer 1990 p. 184.

*Primary Examiner*—Lila Feisee
*Attorney, Agent, or Firm*—Rae-Venter Law Group P.C.

[57] ABSTRACT

Methods and compositions are provided for protecting antigens having a specific epitope associated with Melanoma. The epitope is present in melanoma cells but is essentially absent from melanocytes cites or other human tumor cells. The antibody can be used in diagnostic methods for histochemical detection of human melanoma of various progression stages and in treatment of melanoma.

15 Claims, 3 Drawing Sheets

FIG. 1c   LFRSEDQSIE = LeuPheArgSerGluAspGlnSerIleGlu

HUMAN MELANOMA CELL SPECIFIC ANTIGENS AND ANTIBODIES

INTRODUCTION

1. Field of Invention

The subject invention is concerned with the preparation of antibodies, particularly monoclonal antibodies, to a marker for human melanoma and their use in the diagnosis and therapy of melanoma.

2. Background

Human malignant melanoma arises from a series of stages starting with the harmless mole, going through intermediate stages of radial to invasive growth and ending in the destructive final stage of metastatic melanoma. Melanoma usually resists chemotherapy as well as radiotherapy. Surgery is the most effective treatment. However, for it to be effective, surgery requires early diagnosis which is unfortunately hampered by the lack of accurate markers for melanoma.

Melanoma associated antigens have been found, but they are of little diagnostic value. For example, the nerve growth factor receptor is found in high density on melanoma cells. However, monoclonal anti-nerve growth receptor antibodies are specific for neural crest cell diseases rather than for melanoma alone. Likewise, other melanoma associated antigens against which antibodies have been raised are nonspecific for melanoma cells. Examples are the monoclonal antibodies raised against in vitro grown melanoma cells which are directed against gangliosides or glycoproteins present on the melanoma cells. Both antigens are also found on other cells.

It is therefore of interest to identify a melanoma-associated antigen which is specific for melanoma as compared to normal melanocytes as well as other normal and malignant cells. An antibody raised against such an antigen could be used in the diagnosis and treatment of melanoma.

3. Relevant Literature

U.S. Pat. No. 4,590,071 is directed to a cytotoxic conjugate specific for human melanoma.

SUMMARY OF THE INVENTION

The present invention provides methods and compositions useful for detecting or monitoring primary and metastatic melanomas. The method relies on the detection of an epitope on the melanoma cells which is specific for melanoma cells. The epitope is essentially absent from human melanocytes and malignant human cells other than melanoma cells. The epitope may be found on melanoma cells in tissue biopsies, in melanoma cells in culture, or other sources of melanoma cells. The epitope appears to be located on the surface of the melanoma cells and may be a cell surface receptor. The putative receptor has an apparent molecular weight of 180 kD by western blotting of lysates of a melanoma cell line. Detection of the epitope may be conveniently accomplished by reaction with monoclonal antibodies derived from hybridoma cell line 12f3.2 or antibodies having a similar specificity and determining the formation of specific complexes. The antigens and/or antibodies find use in vitro or in vivo in diagnosis and therapy. Antiidiotypic antibodies may also find use for detecting the presence of antibodies to the antigen in the blood or serum of a human host, as well as use as antigens.

BRIEF DESCRIPTION OF THE DRAWINGS

FIG. 1. (a) Schematic structure of putative mrk receptor tyrosine kinase, SP=signal peptide, TM=transmembrane domain, TK=tyrosine kinase domain, striped boxes=cystine-rich domains, below similarities of various domains to the human epidermal growth factor receptor HER-1 (our own and data from Wittbrodt, et al., 1989); (b) surface values of amino acid residues 340–640 in which the peptide spans amino acids 480–489 (marked in yellow); (c) nucleotide sequence SEQ ID NO:2 and amino acid sequence SEQ ID NO:3 (below) spanning the amino acid sequence from 446–486.

FIG. 2. Immunostaining with mAb 12f3.2 of a) cells from Xiphophorus melanoma cell line PSM; b) frozen section of dorsal fin, positive red staining in prepigment cells (large arrow) which are close to fully differentiated normal pigment cells (small arrows); c) frozen sections from Xiphophorus malignant melanoma, red staining in more spindle-shaped, lightly pigmented and less differentiated pigment cells in peripheral growth areas. Sections were stained with supernatant mAb 12f3.1 diluted 1:50 in PBS and counterstained with Mayer's H. Detection in a) with anti-rat IgG FITC conjugate and in b and c) with avidin-biotin conjugate (ABC kit, Vector Laboratories) and AEC (3-amino-9-ethylcarbazole) as the chromogenic substrate. Magnification: a) 100x, b and c) 250x.

FIG. 3. Immunostaining with mAb 12f3.2 supernatant (1:50 in PBS) of sections from paraffin-embedded a) primary human melanoma; red staining in nests of melanoma cells (arrows) but not in other cells or in 'healthy' skin containing normal melanocytes; b) metastatic human melanoma. Detection and counterstaining as in FIG. 2. Magnification: a) 100x, b) 250x.

DESCRIPTION OF SPECIFIC EMBODIMENTS

Methods and compositions are provided for the detection, identification, and monitoring of melanomas. It has been found that melanomas are characterized by the presence of an about 180 KD protein on the cell surface of a melanoma cell which is immunologically related to an mrk-receptor tyrosine kinase present in the Xiphophorus fish melanoma. Thus, patient samples may be screened for melanoma by assaying for the presence of the protein.

The Xiphophorus fish melanoma model is well established as a model for human malignant melanoma. In both, the melanomas are made up of the same cell type and are of the same developmental origin, the neural crest. The stages of melanoma progression which have been characterized for melanomas in man are similar to those found in fish. One particular type of human melanoma, familial subcutaneous malignant melanoma is clustered in families, thereby indicating a genetic basis. Genes identified in the fish as being relevant to pigment cell development and/or melanoma formation can therefore be used as probes to isolate the human counterpart from genomic or cDNA libraries. Genes can also be used in raising antibodies against antigens found on human melanoma cells.

In this model for human malignant melanoma, several genetic factors can be identified which mediate the progression of a normal melanin bearing pigment cell into a malignant, metastatic melanoma cell. One complex locus encompasses genetic information for the formation and location of macromelanophores and also for melanoma permissiveness. (The term "macromelanophore" refers to the large melanophores found in Xiphophorus which are larger and have more melanin pigment than melanocytes in the human.) To identify oncogene related genes on the chromosome carrying the complex locus, the Xiphophorus fish genome can be screened with conserved oncogene probes. Genetic linkage analysis is then used to identify genes which are closely linked to the complex locus and thus a candidate for any of the encoded information in the complex locus, for example for melanoma permissiveness, and then to differentially screen for those genes found only in cells which produce the pigment cell giving rise to melanomas. Examples of such genes are the erb-B related gene, and the src (Rous sarcoma virus) oncogene.

Genomic and cDNA clones were isolated and partially sequenced; and RNA expression studies carried out to identify genes which are preferentially expressed in tissue containing melanophores and which are highly expressed in the fish melanomas. Using this methodology genes which are specific for melanomatosis pigment cell growth can be identified. The gene product, or a portion thereof can then be used to generate monoclonal antibodies. In order to obtain a highly specific antibody the deduced amino acids encoded by the gene can be evaluated to identify a portion of the expression product most likely to be highly antigenic such as the extracellular domain of a surface receptor.

The sequence can also be evaluated to identify a unique amino acid sequence, i.e., a portion of the polypeptide which is not found in other proteins using data bank comparisons and computer modeling. A peptide consisting of the amino acid sequence and optionally any additional residues desirable for coupling to a carrier for immunization can then be prepared. The oligopeptides combine the desired amino acid sequences in substantially pure form. Thus, usually the subject composition will be at least 80 mole percent, usually at least about 90 mole percent of the particular oligopeptide or mixture of oligopeptides which come within a particular formula.

The subject compounds are made in conventional ways which can be employed for the production of oligopeptides. Techniques include using automatic peptide synthesizers, employing commercially available protected amino acids. Alternatively, recombinant DNA technology may be employed, by synthesizing according to conventional procedures the appropriate nucleotide sequence, joining the sequence to an appropriate replication vector, transforming a host cell and cloning and growing the transformed host cell to produce the oligopeptides of interest which may then be isolated.

For preparation of antibodies, the subject compounds can be conjugated to an immunogenic carrier, for example antigen proteins, to act as a hapten for production of antibodies specific for an epitope on melanoma cells. Various proteins may be employed as antigens which are not endogenous to the host. Commonly employed antigens are the albumins, globulins, keyhole limpet hemocyanin, or the like. Haptenic conjugates to antigens are well known in the literature under and are amply exemplified in a wide variety of patents. See for example, U.S. Pat. Nos. 4,156,081, 4,069,105 and 4,043,989.

The haptenic antigen conjugates may be used in accordance with conventional ways to immunize a mammal, for example, rat, mouse or higher mammal, for example, primate, including human in accordance with conventional procedures. See, for example, U.S. Pat. Nos. 4,172,124, 4,350,683, 4,361,549, and 4,464,465. Hybridomas may be prepared by fusing available established myeloma lines, for example, SP2-0, NS/1, AG8.6.5.3, etc. with peripheral blood lymphocytes, for example, splenocytes or other lymphocytes of the immunized host. The resulting immortalized B-lymphocytes, for example hybridomas, heteromyelomas, EBV transformed cells etc., are then selected, cloned and screened for binding to the subject epitope.

The antibodies obtained and employed may be any one of the classes, such as IgA, IgD, IgE, IgG and IgM, and any one of the subclasses of the various classes. In addition, whole antibodies or fragments of the antibodies may be employed, such as FAB, F(ab)'$_2$, F$_v$, or the like. The subject immortalized B-lymphocytes or other cells, for example T-cells, which provide receptors specific for the subject epitope, may be used as a source of DNA, either genomic or cDNA, for expression of the ligand heavy chains of the receptors in procaryotes or eucaryotes. The resulting products may then be used as receptors for binding to the subject epitopes.

The epitopes may be characterized as being present on melanoma cells and essentially absent from normal melanocytes and malignant cells other than melanoma cells, the epitope binding specifically to the monoclonal antibody 12f3.2 and having an apparent molecular weight of about 180 KDal in the PSM cell line.

Once antibodies are available which are specific for the epitope, the antibody may be used for screening for different antibodies from the same or a different host which bind to the same epitope by employing the subject antibody 12f3.2, secreted by the hybridoma deposited Jan. 27, 1993 with the ATCC and bearing Accession No. HB11252, or antibodies prepared to the epitope which cross-react with 12f3.2. Monoclonal antibody 12f3.2 is secreted by hybridoma cell line 12f3.2.

The antibodies find use in diagnosis, with tissue employing cytology, with lysates of tissue or in detecting the subject epitope in blood or serum. A wide variety of techniques and protocols exist for detecting an antigen in a sample suspected of containing the antigen. Protocols involve a wide variety of labels, which labels include radio-nuclides, enzymes, fluorescers, fluorescer-quencher combinations, chemiluminescers, magnetic particles, and the like. These labels may be directly conjugated to the monoclonal antibody through a variety of covalently bonded linking groups and functionalities. Some of the techniques involve having one of the members of the antigen-antibody complex bound to a support, such as a particle or vessel wall, while other of the assays are performed in solution without a separation step, where uncomplexed label is separated from complexed label. In a number of assays, the antibody need not be labeled, such as in hemagglutination or where anti-immunoglobulin is employed and the anti-immunoglobulin is labeled, so as to provide for indirect labeling of the subject monoclonal antibody. Assays which may be employed includes assays such as ELISA, RIA, EIA, PCR (Frye, et al., Oncogene 4:1153–1157, 1987) and the like.

Generally, it will be necessary to pretreat the tissue sample in some manner prior to performing a screening assay, generally immunoassay. Sample preparation will vary depending on the source of the biological sample. Cell or tumors and other tissue samples may be prepared by lysing the cells. Serum samples typically can be prepared by clotting whole blood and isolating the supernatant in accordance with well known methods.

For diagnosis of melanoma, biopsy specimens are the most likely source of samples for analysis. Conventional immunohistochemical staining techniques may also be used for detecting the epitope in tissue samples. For example, the tissue sample may be fixed in formalin or other standard histological preservatives, dehydrated and embedded in paraffin as is routine in any hospital pathology laboratory. Sections may be cut from the paraffin and mounted on glass slides or the sections may be prepared from cryo-preserved tissue. Alternatively, cytological preparations may be used. For example, cells from the tissue sample may be fixed on a slide, typically by exposure to formalin in a buffer at physiologic pH followed by suspension in acetone and pelleting onto gelatin-coated slides by centrifugation. The cellular antigen may be localized, either by exposure to labeled antibody or by exposure to unlabeled antibody and a labeled secondary antibody. The amount of the cell surface protein or antigen in the sample is directly proportional to the amount of bound label.

Whole body imaging techniques employing radioisotope labels can be used for locating melanomas which have metastasized. The antibodies of the present invention, or fragments thereof, are bound to a suitable radioisotope, typically technetium-99, $^{123}$iodine, $^{125}$iodine, or $^{131}$iodine, or a combination thereof, and administered parenterally. The biodistribution of the label is monitored by scintigraphy, and accumulations of the label may be related to the presence of melanoma cells. Whole body imaging techniques are described in U.S. Pat. No. 4,036,945 and 4,311,688, the disclosures of which are incorporated herein by reference.

Monoclonal antibodies may be used in other ways than binding to the subject epitopic site. Monoclonal antibodies to the epitopic site may in turn be used as antigens for the production of monoclonal antibodies specific for the idiotypic side of the monoclonal antibody to the cell surface receptor, for example 12f3.2. The anti-idiotypic monoclonal antibody may be used to detect the presence of antibodies in a host to the cell surface receptor, where the monoclonal antibody to the cell surface receptor and the physiological fluid to be diagnosed are from the same host. For example, where the monoclonal antibody to the cell surface receptor is a human antibody, then the human monoclonal antibody to the cell surface receptor may be used as an antigen to make monoclonal antibody specific for the human idiotype for the cell surface receptor, which monoclonal antibodies could be used to protect antibodies to the cell surface receptor which may be present in a human physiological fluid, for example blood or serum. The anti-idiotypic monoclonal antibody may be made in any host, for example rodent, more particularly rat or mouse.

In addition, the conformation of the idiotype of the anti-idiotypic monoclonal antibody will resemble the epitope of the cell surface receptor and thus may serve as an antigen in competition with the cell surface receptor epitope. To that extent, the idiotypic monoclonal antibody may serve as a vaccine in inducing an immune response to the cell surface receptor epitope different from the immune response obtained with the cell surface receptor. Furthermore, the anti-idiotypic monoclonal antibody may serve as a reagent as a ligand to be competitive with the cell surface receptor.

The monoclonal antibodies may also be used as a means of purifying the cell surface receptor from melanoma cells, for example in combination with a solid support, to form an affinity matrix.

The specificity of the monoclonal antibodies makes them useful as targeting agents for human melanoma cells. For example, the antibody may be coupled to a cytotoxic agent using methods known to those skilled in the art. For example, see U.S. Pat. No. 4,590,071 and U.S. Pat. No. 5,055,291, which discoveries are incorporated herein by reference. T-cell therapy may also be used, for example see Rosenberg, *New England Journal of Medicine* 316:789, 1987, which disclosure is incorporated herein by reference. Deposit: The hybridoma cell line 12f3.2 has been deposited with the American Type Culture Collection under the conditions by the Budapest Treaty. The deposit was made on Jan. 27, 1993 and has been given accession number HB11252. The address of the depository is 12301 Parklawn Dr. Rockville Md. 20852.

The following examples are offered by way of illustration and not by way of limitation.

EXAMPLE 1

Preparation of Melanoma-Specific Antigen

The Xiphophorus fish genome was screened with conserved oncogene probes to identify oncogeny related genes on the chromosome carrying the complex locus which encompasses genetic information for the formation and location of macromelanophores and melanoma permissiveness.

In an attempt to isolate the genes of the major loci oncogene probes were used to identify restriction fragment polymorphisms (RFLPs) as markers for these loci. RFLPs were found for genes similar to the src, erb-B gene: the latter gene appears to be very closely linked to the sex linked pigmentary locus and is considered to be a candidate gene for some of the information contained in this locus.

Using the erb-B oncogene probe, a genomic phage library was screened and several positive clones were isolated. The clones were characterized by restriction enzyme mapping, which yielded five clones that encompassed the same restriction fragments as those identified in genomic southern blots using the erb-B probe. Probes from these Xiphophorus clones were used to screen two cDNA libraries yielding twenty clones, one of which carried an insert corresponding to the RNA fragment detected in a Northern blot analysis of the RNA from the PSM cell line. Restriction mapping of this clone as well as partial sequencing revealed that the identified gene is probably identical with the published Xmrk gene (Wittbrodt et al., 1989, Nature 341:415–421).

Differential PCR analysis with total RNA from testis, ovary, liver, kidney, brain, eye, skin, skin areas with melanophores, and melanomas using mrk-specific primers revealed that mrk is preferentially expressed in tissue containing melanophores and is highly expressed in the melanomas. This and the fact that this gene is only found in fish that can produce the cells giving rise to melanoma make it a very specific gene for melanomatosis pigment cell growth.

Figure 1A:
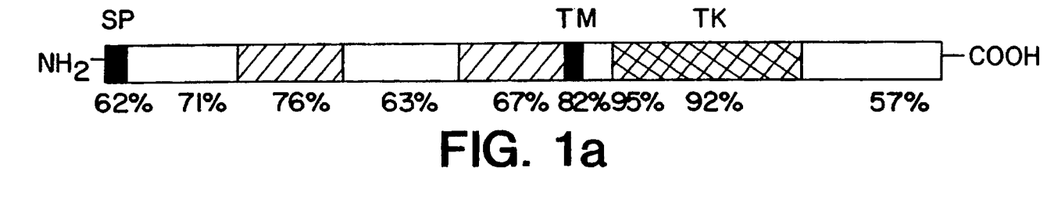
Figures 1B, 1C:
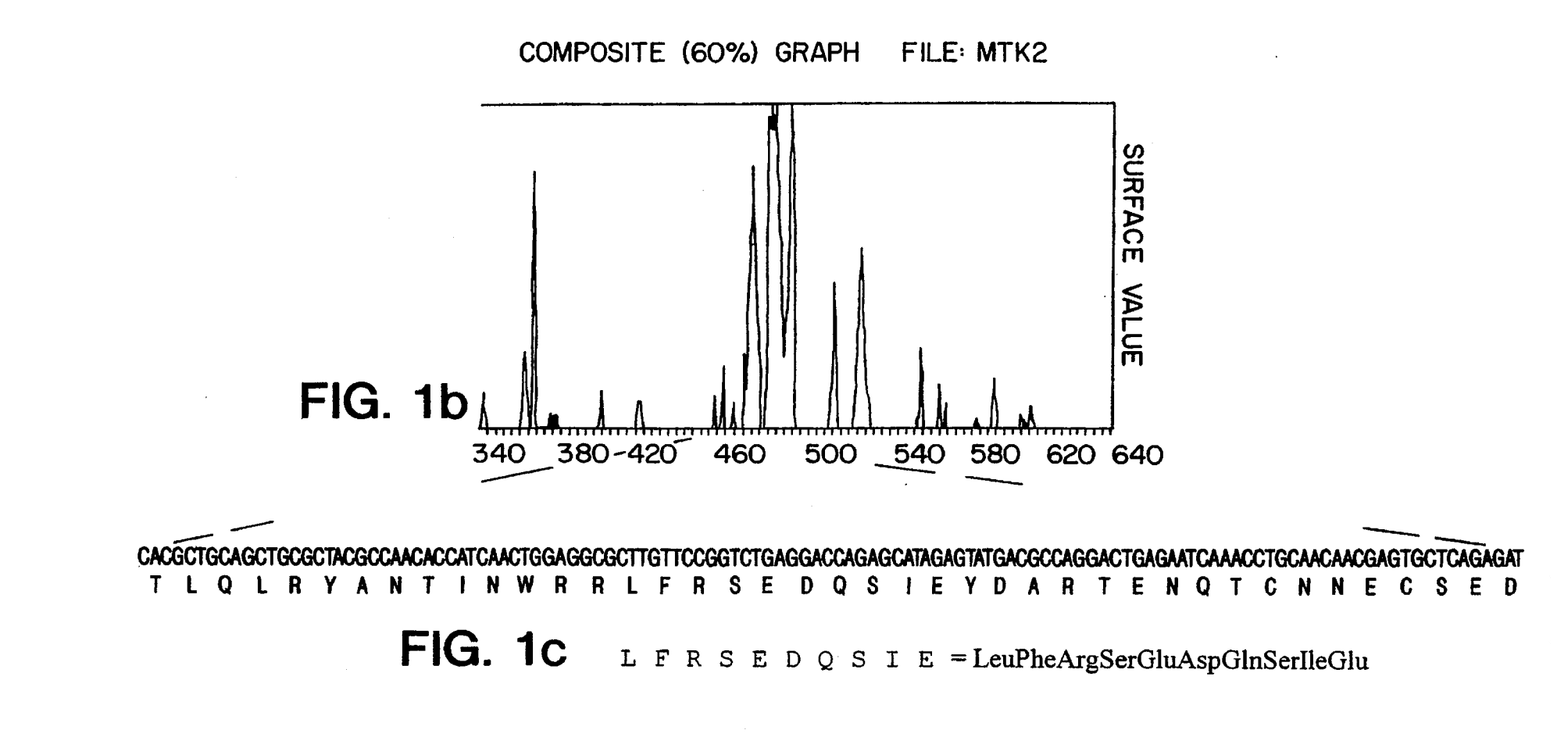

Comparisons of the mrk sequence were done with sequences contained in the latest available Genbank and EMBL genebank computer programs and its deduced amino acids showed that the putative protein belongs to the family of receptor-tyrosine kinases consisting of an extracellular domain, a transmembrane domain and a cytoplasmic tyrosine kinase domain; the protein is most closely related to the human epidermal growth factor receptor (FIG. 1). The cytoplasmic tyrosine kinase domains are highly conserved domains and the transmembrane domain is unlikely to be highly antigenic. Therefore, the extracellular domain was further evaluated to find a portion of that domain which is not found in other proteins and for which high antigenicity can be assumed.

A computer modelling (Surfaceplot-Synthetic Peptides, Inc.; see Parker et al., Biochem 25:5426–5432, 1985) of the putative mrk-receptor protein was done for the prediction of antigenicity of portions of this protein. An exposed sequence of 10 amino acids SEQ ID NO:4 (L-F-R-S-E-D-A-S-I-E) (SEQ ID NO:1) of the extracellular domain met this demand. The amino acid sequence of this portion of the mrk-protein also avoids any similarity to the amino acid sequences of the true epidermal growth factor receptor of fish or human origin and according to an extensive search in the gene/protein data banks, no significantly similar amino acid sequences exist in other proteins. This sequence, therefore, appears to be rather specific for the novel receptor; a peptide was therefore synthesized and used for the generation of antibodies (FIG. 1). For coupling to the hapten, the peptide was synthesized with a cysteine residue at the N-terminus. The peptide was coupled to the hapten KLH (keyhole limpet hemocyanin, Pierce Chemical Co.), via SMCC (succinlmidyl 4-(N-malelmldomethyl)cyclohexane-1 carboxylate, Pierce Chemical Co.) (see Sutcliffe et al., 1980; Sela, Synthetic Vaccines Vol. 1 R. Amon (Ed.), CRC Press, Boca Raton, Fla., pp. 85–92, 1987).

EXAMPLE 2

Preparation of Antibodies to Mrk-receptor Protein Fragment

Immunization

The hapten-peptide conjugate was mixed 1:1 with Freund's complete adjuvant and 0.8 ml injected intraperitoneally (ip) into each of three Fischer rats (125–150 g body weight) at a concentration of 0.5 mg/ml. After 14 days a second ip injection of the KLH-peptide conjugate was given, and then 4 times at a 14 days interval the uncoupled peptide at a concentration of 0.5 mg/ml was injected. At that time a positive immunoresponse of the serum of the rats was monitored by standard ELISA using cells from our Xiphophorus fish melanoma cell line (PSM line) which show a high expression of the mrk gene as positive and our Xiphophorus fibroblastoid cell line (XGI line) as negative control as was the rat preimmune serum; staining was done using goat anti-rat IgG (H+L) (Jackson Immun. Lab.) as secondary antibody conjugated to horseradish peroxidase and OPD (o-phenylenediamine dihydrochloride, Sigma) as the chromogenic substrate. Another ip immunization with the peptide at a higher concentration (0.8 mg/ml) was then done followed by an intravenous injection of the peptide (0.8 mg/ml) without Freund's adjuvant 3 weeks later. Four days later monoclonal antibody production was started by fusing $4\times10^8$ spleenocytes from the rat which gave the strongest immunresponse to $0.8\times10^8$ SP2/O mouse myeloma cells. Fourteen 96-well microtitre plates were seeded with a spleen cell density of $1.25\times10^3$ cells/well. Cells were grown for 7 days in HAT-DMEM (TFL Media Preparation Service, Vancouver, B.C.) supplemented with 50 u/ml of Interleukin-8.

Isolation of clones

Screening of monoclonal producing hybridoma cells was done on terazaki plates coated with cells fixed in 0.05% glutaraldehyde from the PSM melanoma cell line as positive control and as negative controls with cells from the XGI cell line, from a gonadal cell line of trout, with fibroblasts and bone marrow cells from human; staining was done as noted above. Cells from 28 wells which yielded a positive signal with the PSM cells were transferred from the microtitre plates into 1 ml of HT-DMEM in 24-well plates and after 3–6 days plated in methylcellulose. Isolation of individual pure hybridoma clones was done by picking at least 12 individual colonies derived from the original positive cells, transferring them into 96well microliter plates and testing again for positive reactivity with the PSM cells and also with the peptide; as negative controls the cells mentioned above were also tested. We isolated three clones which produced monoclonal antibodies that reacted positively with the peptide and the fish melanoma cell line but exhibited no reactivity with the other cells.

Two other clones, 10A3 and 3B7 reacted less strongly and three clones, 5C1, 6E4, and 14C7, reacted not only with the peptide and the fish melanoma cell line but also with a trout cell line, making them more general.

Typing of Antibody

Figure 2A:
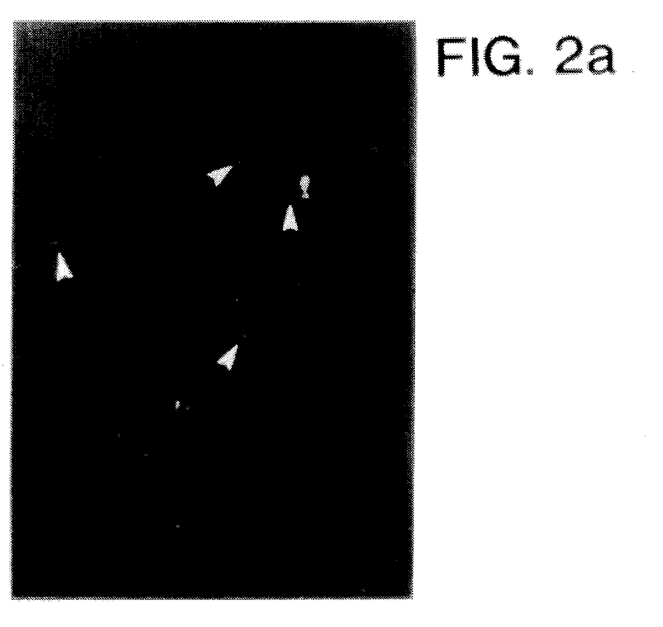

Supernatants of the three positive hybridoma clones were subsequently reacted with cultured PSM as well as XGI cells fixed on the culture dishes with 4% paraformaldehyde (90 min, RT); staining was done using anti-rat 2nd-Ab conjugated to horseradish peroxidase (Jackson Immun. Lab.) and DAB (3,3'-diaminobenzidine, Sigma) as chromogenic substrate or with goat anti-rat F(ab)$_2$ FITC coupled secondary Ab (Cappel). The clone 12f3.2 produced the strongest signal with the PSM cells and we thus concentrated on it first. Typing of this mAb using a Bio-Rad kit which is a mouse typing kit but also has cross-reactivity with rat Abs revealed that the mAb of the hybridoma alone 12f3.2 is an IgG$_1$ (k). Immunostaining of cells from Xiphophorus PSM melanoma cell line To further verify the specificity and identify the location of the antigen recognized by the peptide-specific mAb, cultured cells of the PSM cell line were fixed and stained (see above) with supernatants of the mAb producing clone 12f3.2. The PSM line contains all stages of pigment cell differentiation; spindle-shaped premelanocytes, young melanocytes with fine few dendrites, polydendritic adult melanocytes, and finally also the large melanophores with broad dendrites and fully loaded with the brown-black melanin pigment. Staining however, was only found in the younger stages, the melanocytes, at the contact sites of their dendrites, on the edges concentrated in spots and in areas where the cells narrow towards the dendrites. This staining pattern is typical for a cell surface receptor or cell contact type antigen. This is in keeping with data we have deduced from the nucleotide sequence, i.e. that the putative mrk protein is a cell surface receptor. This staining behavior is more prominent in vitally stained cells and using the FITC coupled 2nd anti-rat IgG antibody (FIG. 2e).

mAb reacts with pigment cells from normal and melanoma tissue in Xiphophorus

Figure 2B:
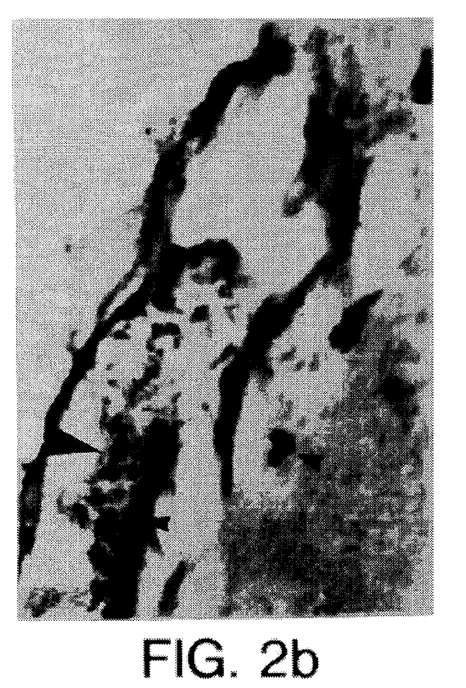
Figure 2C:
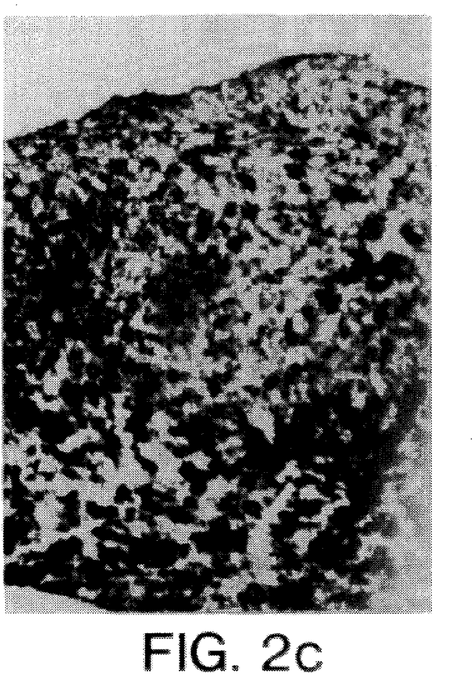

While the culturing of melanoma cells can yield valuable information the classification of the disease state must be done on sectioned material. In order to test the suitability of the produced mAb 12f3.2 cross-sections from frozen as well as paraffin embedded material were stained using the avidinbiotin procedure (ABC staining kit, Veotor Lab.) and AEC(3-amino-9-ethyloarbazole, Sigma) as chromogenic substrate. So far we have obtained with mAb 12f3.2 supernatant (1/50 in FBE) a positive signal in frozen positioned and acetone-fixed Xiphophorus dorsal fin material which contains in the dermis fully differentiated melanophores and immature, non-pigmented precursors underlying the differentiated cells. Very interestingly, staining was not observed in the melanophores (FIG. 2b. small arrows) but in the precursors (FIG. 2b. large arrow). Sections of melanoma tissue stained positive in areas representing tumour growth and which are composed of spindle-shaped, lightly pigmented cells (upper area in FIG. 2c).

mAb stains human melanoma cells but not normal melanocytes in vitro

The encouraging results of the detection of melanoma cells from our model led us to further test the mAb by immunostaining human melanoma cell lines derived from patients from whom B-cells were also available as a control. The cells in the culture dishes were fixed with 0.4% paraformaldehyde for 30 min. at RT and then immunostained as described above for cultured fish cells. All three melanoma cells lines KZ-2,-13,-26 stained positively but each in a characteristic way. The spindle-shaped, dendritic KZ-2 cells exhibited an evenly distributed staining with some spots of more concentrated staining, the dendritic to polydendritic KZ-13 cells exhibited the staining in the cell's body and at the start of the dendrite, and the larger KZ-26 cells which have broad dendrites and tend to conglomerate show strong staining in the centers of these concentrations presumably where their dendrites contact each other. The B-cells of the patients did not show any staining at all nor did the cultured melanocytes derived from human foreskin. The history of the human melanoma cells are not quite clear with regard to classification of the described stages above, i.e. radial, vertical growth phase, metastatic phase. However, the KZ-2 cells show the fastest, KZ-13 slower and the KZ-26 cells an even slower growth. Thus, the mAb appears to yield a characteristic staining of melanoma cells of various growth potential.

mAb reacts with human melanoma tissue

Figure 3A:
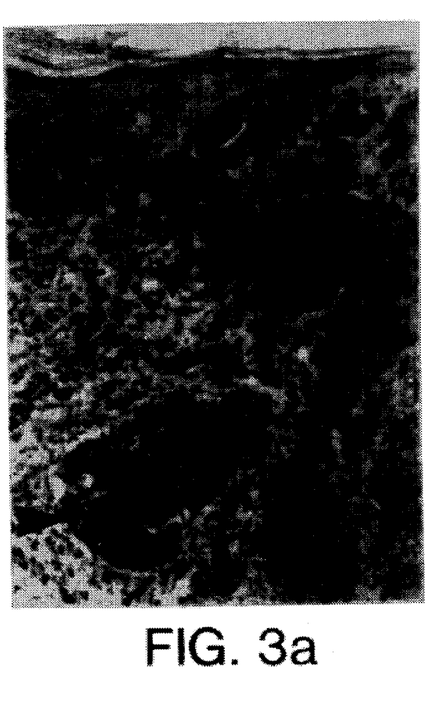
Figure 3B:
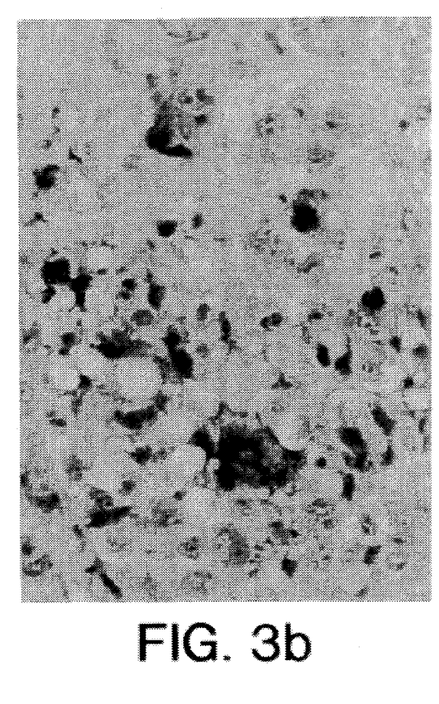

The most important question to answer was whether or not the mAb recognizes human melanoma tissue. Sections from three primary and four metastatic acetone-fixed and paraffin-embedded human melanoma specimens obtained from six different patients were stained with the mAb 12f3.2 supernatant diluted 1/50 with PBS as described above for the sections of fish tissue; all melanomas showed positive staining. In the primary melanomas nests of positive melanoma cells were observed (FIG. 3a, arrows) while in the metastatic tumors the positive cells were more dispersed (FIG. 3b); two of the metastatic tumors of the same patient showed a very strong staining that appeared as grainy spots indicative of antigen located on the surface of the melanoma cells (FIG. 3b). The healthy skin including the melanocytes as well as other cell types within the melanoma, e.g. lymphocytes, did not show any staining.

Identification of melanoma related characteristics by western blotting

Another possibility to identify melanoma specificity is to analyze electrophoretically separated proteins on nitrocellulose blots. Therefore cells of the PSM and KZ-13 melanoma cell lines were lysed and separated and blotted according to standard conditions and the blots immunostained with the mAb. Only the melanoma showed a positive signal; the PSM cells revealed a weak signal at 180 KD which would be expected from the predicted amino acid sequence and a strong signal of approx. 70 KD which may be a degradation product of the activation and signal transduction of the mrk-receptor tyrosine kinase (see Ullrich and Schlessinger, Cell 61: 203–212, 1990). Signals in very similar size ranges were detected in the human melanoma cells. No signal at all was found in lysates derived from the control XGI cell line which is to be expected as these cells do not express the mrk gene.

A rat monoclonal antibody was produced against a synthetic peptide which represents a putative highly antigenic portion of a novel receptor tyrosine kinase protein. The protein is coded by a melanoma pigment cell specific gene which was cloned from Xiphophorus fish. Xiphophorus represents an animal melanoma model which is well established as a model for human melanoma formation.

The mAb recognizes the prepigment cells in situ, the undifferentiated melanocytes of a Xiphophorus melanoma cell line and also the melanoma cells in growth areas of Xiphophorus melanomas. It also reacts characteristically with cultured human melanoma cells of different growth potential and with primary and metastatic secondary melanomas in situ. The staining pattern of secondary melanoma cells has a grainy appearance. The mAb does not react with normal human cultured melanocytes nor with those that are located in the normal skin adjacent to the melanomas. In conclusion, the mAb has the potential to become a tool for histochemical characterization of melanoma cells in patients and for treatment.

In accordance with the subject invention, antibodies and their complementary antigens are provided which is specifically related to human melanoma. The antigens are believed to be cell surface receptors, related to a mrk-receptor tyrosine kinase, where the whole mrk-receptor or fragments thereof, including the epitopic site of interest, may be employed by themselves or in conjunction with complementary antibodies as reagents in diagnostic assays. In addition, the antibodies may find use in vivo imaging and therapy. The antibodies can also be used in such homology of biopsy specimens with the detection of the presence of the antigen and the tissue. The presence of the tumor marker may be found in the blood as indicative of the existence of a melanoma. Thus, it may be feasible to not only detect at a early stage the existence of melanoma cells in a human host, but further, to detect their specific location in the human host. In addition, antibodies to the antigen may be detected as indicative of the existence of melanoma or its recurrence.

All publications including patent applications mentioned in this specification are indicative of the level of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be apparent to one of ordinary skill in the art that many changes in modifications can be made thereto without deporting from the spirit or scope of the appended claims.

What is claimed is:

1. A hybridoma cell line producing monoclonal antibodies specific for an epitope which (1) is present on the surface of human melanoma cells and is essentially absent from melanocytes and malignant cells other than melanoma cells and (2) has an apparent molecular weight of 180KDal in the PSM cell line.

2. A hybridoma cell line 12f3.2, having ATCC accession number HB11252.

3. A monoclonal antibody which binds to (a) an epitope which is present on the surface of human melanoma cells and is essentially absent from (1) melanocytes and (2) malignant cells other than melanoma cells.

4. A monoclonal antibody produced by a hybridoma which produces monoclonal antibodies specific for an epitope which is present on the surface of human melanoma cells and is essentially absent from (1) melanocytes and (2) malignant cells other than melanoma cells, wherein said hybridoma is produced by fusing lymphocytes from a mammal immunized with an immunogen which consists essentially of the amino acid sequence depicted in SEQ ID NO:1 with immortalized B-cells in vitro.

5. The monoclonal antibody according to claim 4, wherein said monoclonal antibody is produced by hybridoma cell line 12f3.2, having ATCC accession number HB11252.

6. A monoclonal antibody fragment of an antibody according to claim 4, said fragment being specific for an epitope which is recognized by the monoclonal antibody according to claim 4 wherein said epitope is present on the surface of human melanoma cells and is essentially absent from (1) melanocytes and (2) malignant cells other than melanoma cells.

7. The monoclonal antibody according to claim 6, labelled with a label capable of providing a detectable signal.

8. A method for producing monoclonal antibodies having the property of distinguishing human malignant pigmented cells from non-malignant pigmented cells by binding to the surface of said malignant cells and exhibiting substantially no binding to said non-malignant cells, said method comprising:

(a) fusing lymphocytes from a mammal immunized with an immunogen which consists essentially of an amino acid sequence depicted in SEQ ID NO: 1 with a fusion partner comprising an established myeloma cell line to produce hybridomas;

(b) cloning said hybridomas to produce individual clones;

(c) screening said clones for those producing monoclonal antibodies having the property of distinguishing malignant pigmented cells by binding to said malignant cells and exhibiting substantially no binding to said non-malignant cells to identify producing clones; and (d) growing said producing clones whereby said monoclonal antibodies are produced.

9. An antibody which binds specifically to a peptide having the amino acid sequence depicted in SEQ ID NO:1.

10. The antibody according to claim 9, wherein said antibody is a monoclonal antibody.

11. A hybridoma cell line which produces an antibody according to claim 10.

12. The hybridoma cell line according to claim 1, wherein said epitope is present on an antigen having an apparent molecular weight of 180KDal in the PSM cell line.

13. A monoclonal antibody produced by a hybridoma cell line according to claim 12.

14. The antibody produced according to the method of claim 8.

15. A method for producing antibodies in a host mammal to an epitope which is present in the extracellular domain of the Xmrk-receptor protein of Xiphophoros in a host mammal, said method comprising:

immunizing said host mammal with a composition comprising an antigen which consists essentially of a peptide having the amino acid sequence depicted in SEQ ID NO:1.

* * * * *

UNITED STATES PATENT AND TRADEMARK OFFICE
CERTIFICATE OF CORRECTION

PATENT NO. : 5,605,831  
DATED : Feb. 25, 1997  
INVENTOR(S) : Juergen R. Vielking Page 1 of 2

It is certified that error appears in the above-identified patent and that said Letters Patent is hereby corrected as shown below:

Column 2, lines 15, 18-19, 43, 46, and 67, italicize "Xiphophorous".

Column 2, line 41, change "KD" to --kD--.
Column 3, line 3, italicize "Xiphophorous".
Column 3, line 11, italicize "erb".
Column 3, line 12, italicize "src".
Column 5, line 41, change "protect" to --detect--.
Column 6, line 25, insert, after "erb-B gene" and before the colon,
   --(Vielkind and Dippel, Canadian Journal of Genetics & Cytology, Vol. 26: 607-614, 1984--
Column 6, lines 16 and 34, italicize "Xiphophorous" at each occurrence.
Column 6, line 40, italicize "Xmrk".
Column 6, lines 25, 29, and 34, italicize "erb" at each occurrence.
Column 6, line 25, italicize "src".
Column 6, lines 44, 45, 50, and 66, italicize "mrk" at each occurrence.
Column 7, line 2, change "(L-F-R-S-E-D-A-S-I-E)" TO --(L-F-R-S-E-D-Q-S-I-E)--.
Column 7, lines 5 and 23, italicize "mrk" at each occurrence.

UNITED STATES PATENT AND TRADEMARK OFFICE
CERTIFICATE OF CORRECTION

PATENT NO. : 5,605,831
DATED : Feb. 25, 1997
INVENTOR(S) : Juergen R. Vielking

It is certified that error appears in the above-identified patent and that said Letters Patent is hereby corrected as shown below:

Column 7, line 16, change "succinlmidyl" to --succinimidyl--.
Column 7, line 40, change "IgG" to --IgG--.
Column 7, line 49, change "immunresponse" to --immune response--.
Column 7, line 67, change "96well microliter" to --96-well microliter--.
Column 7, line 16, change "malelmldomethyl" to --maleimidometyl--.
Column 7, lines 35-36 and 37-38, italicize "Xiphophorous".
Column 8, line 14, change "90" to --20--.

Column 8, lines 24, 46 and 56, italicize "Xiphophorous" at each occurrence.
Column 8, line 41, italicize "mrk".
Column 9, line 9, the comma in "staining, the dendritic" should be a semi-colon.
Column 9, lines 49 and 51, "KD" should read --kD--, at each occurrence.
Column 9, line 53, italicize "mrk".

Signed and Sealed this

Twenty-fourth Day of February, 1998

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:

```
              ( A ) LENGTH: 10 amino acids
              ( B ) TYPE: amino acid
              ( D ) TOPOLOGY: linear ( i i ) MOLECULE TYPE: protein ( x i ) SEQUENCE DESCRIPTION: SEQ ID NO: 1:

Leu  Phe  Arg  Ser  Glu  Asp  Gln  Ser  Ile  Glu
 1              5                         10

( 2 ) INFORMATION FOR SEQ ID NO:2:

( i ) SEQUENCE CHARACTERISTICS:
              ( A ) LENGTH: 124 base pairs
              ( B ) TYPE: nucleic acid
              ( C ) STRANDEDNESS: double
              ( D ) TOPOLOGY: linear ( i i ) MOLECULE TYPE: DNA (genomic)

( i x ) FEATURE:
              ( A ) NAME/KEY: CDS
              ( B ) LOCATION: 2..124

( x i ) SEQUENCE DESCRIPTION: SEQ ID NO:2:

C  ACG  CTG  CAG  CTG  CGC  TAC  GCC  AAC  ACC  ATC  AAC  TGG  AGG  CGC  TTG          46
   Thr  Leu  Gln  Leu  Arg  Tyr  Ala  Asn  Thr  Ile  Asn  Trp  Arg  Arg  Leu
    1              5                        10                        15

TTC  CGG  TCT  GAG  GAC  CAG  AGC  ATA  GAG  TAT  GAC  GCC  AGG  ACT  GAG  AAT       94
Phe  Arg  Ser  Glu  Asp  Gln  Ser  Ile  Glu  Tyr  Asp  Ala  Arg  Thr  Glu  Asn
                    20                       25                       30

CAA  ACC  TGC  AAC  AAC  GAG  TGC  TCA  GAG  GAT                                    124
Gln  Thr  Cys  Asn  Asn  Glu  Cys  Ser  Glu  Asp
                35                       40

( 2 ) INFORMATION FOR SEQ ID NO:3:

( i ) SEQUENCE CHARACTERISTICS:
              ( A ) LENGTH: 41 amino acids
              ( B ) TYPE: amino acid
              ( D ) TOPOLOGY: linear ( i i ) MOLECULE TYPE: protein ( x i ) SEQUENCE DESCRIPTION: SEQ ID NO:3:

Thr  Leu  Gln  Leu  Arg  Tyr  Ala  Asn  Thr  Ile  Asn  Trp  Arg  Arg  Leu  Phe
 1              5                        10                       15

Arg  Ser  Glu  Asp  Gln  Ser  Ile  Glu  Tyr  Asp  Ala  Arg  Thr  Glu  Asn  Gln
                20                       25                       30

Thr  Cys  Asn  Asn  Glu  Cys  Ser  Glu  Asp
                35                       40
```